United States Patent
Dong et al.

(10) Patent No.: US 9,437,017 B2
(45) Date of Patent: Sep. 6, 2016

(54) METHOD AND APPARATUS FOR METAL ARTIFACT ELIMINATION IN A MEDICAL IMAGE

(71) Applicant: General Electric Company, Schenectady, NY (US)

(72) Inventors: Shuqin Dong, Beijing (CN); Jiaqin Dong, Beijing (CN); Shuo Li, Beijing (CN); Jiang Hsieh, Waukesha, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 14/522,783

(22) Filed: Oct. 24, 2014

(65) Prior Publication Data
US 2015/0117740 A1    Apr. 30, 2015

(30) Foreign Application Priority Data
Oct. 31, 2013    (CN) .......................... 2013 1 0532522

(51) Int. Cl.
| | | |
|---|---|---|
| G06K 9/00 | (2006.01) | |
| G06T 11/00 | (2006.01) | |
| A61B 6/00 | (2006.01) | |
| G06T 5/00 | (2006.01) | |

(52) U.S. Cl.
CPC ........... *G06T 11/008* (2013.01); *A61B 6/5258* (2013.01); *G06T 5/005* (2013.01); *G06T 2207/10081* (2013.01); *G06T 2207/30004* (2013.01)

(58) Field of Classification Search
None
See application file for complete search history.

(56) References Cited

U.S. PATENT DOCUMENTS

| | | | | |
|---|---|---|---|---|
| 7,340,027 | B2* | 3/2008 | Timmer ................ | G06T 11/005 378/4 |
| 2005/0123215 | A1* | 6/2005 | Man ..................... | G06T 11/005 382/275 |
| 2011/0081071 | A1* | 4/2011 | Benson ................ | G06T 11/005 382/154 |

OTHER PUBLICATIONS

"CT metal artifact reduction method correcting for beam hardening and missing projections"; Authors Joost M. Verburg and Joao Seco; Published Apr. 18, 2012 in Physics in Medicine and Biology.
"Reduction of computed tomography metal artifacts due to the Fletcher-Suit applicator in gynecology patients receiving intracavitary brachytherapy"; Authors John Roeske, Christina Lund, Charles Pelizzari, Xiaochuan Pan, Arno Mundt; Aug. 2003.
"Minimizing Clip Artifacts in Multi CT Angiography of Clipped Patients"; Authors van der Schaaf, van Leeuwen, Vlassenbroek, Velthuis; Published Jan. 2006 issue of AJNR.
"Adaptive Normalized Metal Artifact Reduction (ANMAR) in Computed Tomography", Authors Esther Meyer, Rainer Raupach, Bernhard Schmidt, Andreas H. Mahnken, and Marc Kachelriess, Published 2011 IEEE Nuclear Science Symposium Conference Record, pp. 2560-2565.

* cited by examiner

*Primary Examiner* — Hadi Akhavannik
(74) *Attorney, Agent, or Firm* — GE Global Patent Operation

(57) ABSTRACT

A method and apparatus for metal artifact elimination in a medical image. The method includes: obtaining a medical image to be processed; determining whether or not a metal region is contained in the medial image; and performing artifact elimination processing to the medical image when metal regions are contained in the medical image and a metal density value of one of the metal regions is greater than or equal to a preset density value.

8 Claims, 5 Drawing Sheets

After the boundary smoothing processing

Before the artifact elimination
processing after the

After the artifact elimination processing

After the boundary smoothing processing

METHOD AND APPARATUS FOR METAL ARTIFACT ELIMINATION IN A MEDICAL IMAGE

TECHNICAL FIELD

Embodiments of the present invention relate to the field of image processing, and in particular, to a method and apparatus for metal artifact elimination in a medical image.

BACKGROUND ART

Computed Tomography (CT) is one of the most important means for medical diagnosis currently. According to the difference in absorption and transmittance rate of X-ray of different human tissues, a highly sensitive instrument is used to measure a human body and then the data acquired from the measurement is input to a electronic computer, which then processes the data and obtains a cross-sectional or three-dimensional image of the part of human body under detection (i.e. CT imaging technology), so as to find any tiny lesion in any part within the body.

However, in the process of CT imaging, a metal object on the patient body, such as a false tooth or surgically implanted metal object will cause a change in the hardness of the X-ray beam, which results in a metal artifact. Since occurrence of a metal artifact influences the recognition of pathologic analysis after the CT imaging, the determination on lesion is thus inaccurate. Therefore, there have been medical image processing methods for the purpose of metal artifact elimination. However, after artifact elimination processing through the methods in the prior art, a new artifact is usually introduced into the image and the boundary of a metal region will be blurred.

The methods for artifact elimination in the prior art perform an overall processing to a medical image where a metal object is contained according to the presence of the metal object is detected, so that a region where no artifact is contained in the medical image or a region where the artifact is insufficient to affect the definition of the medical image also undergoes the same artifact elimination processing as an artifact region that actually needs to be processed. This results in over-intensification of the image for an artifact region that does not necessary to be processed, whereby a new artifact is generated. In the meanwhile, it may also result in blurring of a boundary of a metal region thereof. There is a solution for boundary blurring in the prior art, that is, processing all metal object regions without considering an artifact portion in the surrounding or other positions, as a result, the brightness of the display of the metal object portion is increased to cover the metal artifact. The result of such processing is that the boundary of a metal region is still not clear enough and the whole CT image is still excessively modified. Therefore, the methods in the prior art still fail to achieve proper artifact elimination, instead, a new artifact is generated and the boundary of metal is still not clear enough. Furthermore, the methods in the prior art fails to enhance the effect of distinguishable lesion in an original medical image, besides, application cost increases.

Thus, it is necessary to provide a new method and apparatus for metal artifact elimination in a medical image to enhance the imaging quality.

SUMMARY OF THE INVENTION

An embodiment of the present invention provides a method for metal artifact elimination in a medical image, including: obtaining a medical image to be processed; determining whether or not a metal region is contained in the medial image; and performing artifact elimination processing to the medical image when metal regions are contained in the medical image and a metal density value of one of the metal regions is greater than or equal to a preset density value.

Another embodiment of the present invention provides an apparatus for metal artifact elimination in a medical image, including: an obtaining module for obtaining a medical image to be processed; a metal region determining module for determining whether or not a metal region is contained in the medial image; and a first artifact eliminating module for performing artifact elimination processing to the medical image when metal regions are contained in the medical image and a metal density value of one of the metal regions is greater than or equal to a preset density value.

DESCRIPTION OF THE DRAWINGS

Embodiments of the present invention are described in combination with the figures for better understanding of the present invention, wherein.

DETAIL DESCRIPTION

Figure 1:
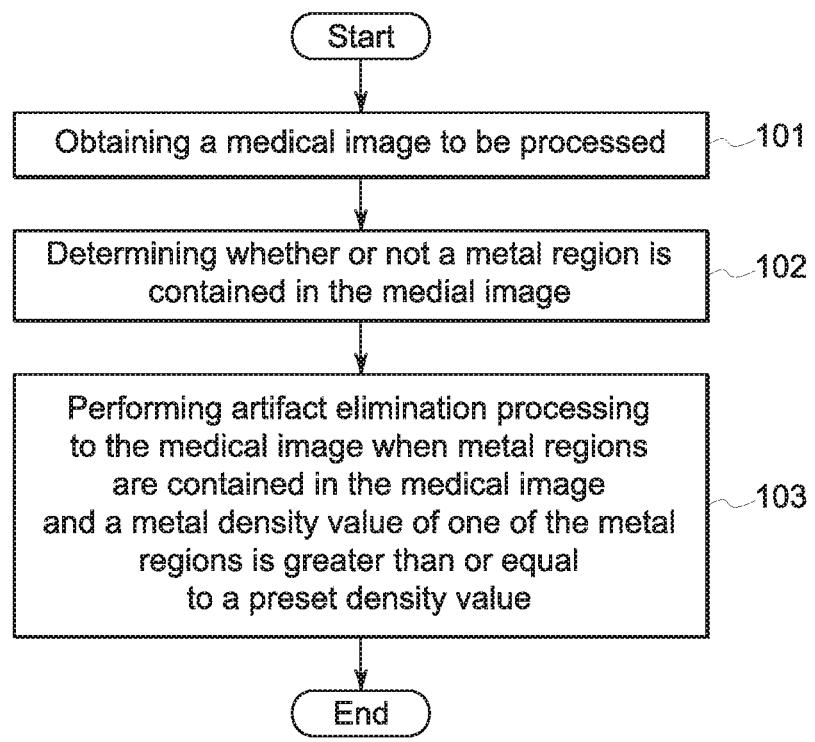
FIG. 1 shows a flow chart of an embodiment of the method for metal artifact elimination in a medical image according to the present invention.

The Detail Description is described in the following part. It should be pointed out that the Description cannot give detailed depiction to all features in the actual implementations in the specific depiction process of the implementations for the purpose of conciseness. It should be understood that in the actual implementing process of any one implementation, just as in the process of any engineering project or design project, in order to realize the specific objective of the developer and to satisfy system-related or commercial-related restriction, various specific decisions may often be made, which may also result in a change from one implementation to another implementation. Besides, it could be understood that although the effort in the developing process may be complicated and long, for those skilled in the art related to the field of the contents disclosed by the present invention, some design, manufacturing or production, etc. on the basis of the technical contents disclosed herein are merely conventional technical measures and the disclosure of the present invention should not be deemed to be insufficient.

Unless otherwise defined, the technical terms or scientific terms used in the Claims and Description should have usual meanings that can be understood by those skilled in the art. It should be understood that the terms "first", "second" and similar terms used in the Claims and Description do not indicate any sequence, number or significance, but only for distinguishing different components. It should be noted that the term "a" or "an" or a similar term does not means a limitation on number, but means at least one; the term "comprising" or "including" and the like only means the element or component prior to the term "comprising" or "including" contains the element, component or equivalent element listed following the term "comprising" or "including", but does not exclude other elements or components. The term "connecting" or "connecting with" and the like is not limited to physical or mechanical connection, or to direct or indirect connection.

In an embodiment of the present invention, a determining process is added prior to the artifact elimination processing, that is, according to a metal property, such as metal density or size, of a metal region in a medical image, a pre-determination is made on whether or not it is required to perform artifact elimination processing to the medical image. The artifact elimination processing is performed only when the processing is required, otherwise, processing is not performed. In this way, unnecessary processing in the process of artifact elimination can be avoided, and the possibility of generating a new artifact is reduced, whereby fast processing of a metal artifact in a medical image is realized so that the precision of medical syndrome scanning is enhanced. Specifically, when it is determined that a metal density value of one of metal regions in a medical image is greater than or equal to a preset density value, artifact elimination processing is performed to the medical image. Besides, when it is determined that a metal density value thereof is smaller than a preset density value, further determination is made on whether or not artifact elimination processing is performed to the medical image in combination with the size of the metal region so as to ensure the reasonability and precision of the artifact elimination processing.

Furthermore, a boundary region of the metal region is determined adaptively based on the size (ratio) of metal within a particular region so as to determine a boundary region more accurately and to perform more accurate boundary smoothing processing to the metal region. In this way, influence on analysis of a medical image caused by boundary blurring resulted from artifact processing can be avoided.

To make the purpose, technical solution and advantages of the present invention clearer, a clear and complete description of the technical solution of the present invention will be given hereinafter in combination with specific embodiments and corresponding figures. Obviously, the embodiments being described herein are only a part of, rather than all of the embodiments of the present invention. Based on the embodiments in the present invention, all other embodiments obtained by those skilled in the art without creative work shall fall within the scope of the present invention.

According to an embodiment of the present invention, a method for artifact elimination processing in a medical image is provided.

Referring to FIG. 1, FIG. 1 shows a flow chart of an embodiment of the method for metal artifact elimination in a medical image according to the present invention.

As shown in FIG. 1, in step 101, obtaining a medical image to be processed, wherein the obtained medical image can be a CT, B ultrasonic, magnetic resonance imaging (MRI) and angiography medical image to be scanned and imaged, but not limited to the aforesaid types of medical processing images.

In step 102, determining whether or not a metal region is contained in the medical image. According to an embodiment of the present invention, it is determined whether a pixel value of a pixel point in a medical image is greater than a preset threshold value, and pixels exceeding the preset threshold value are picked out. A region formed by these pixel points exceeding the threshold value is a metal region.

In step 103, performing artifact elimination processing to the medical image when metal regions are contained in the medical image and a metal density value of one of the metal regions is greater than or equal to a preset density value.

In the process of scanning a medical image, the final scanning result of the medical image is often affected because a metal object (e.g. a metal false tooth or an alloy bone) is present on the patient body. However, not all metal regions affect the final scanning result of the medical image. Thus, a determination on whether or not artifact elimination processing is required to the medical image containing the metal region based on a specific metal property within the metal region.

Specifically, in a medical image containing a metal region, if the metal density is higher, a high image gray value will be generated. Since the gray value is too high, it will cause the brightness generated thereby in the image to be too great and the surrounding non-metal regions will thus be covered, and the overall effect of medical image generation will be affected. On the contrary, if the image gray values generated by metal density are even and will not affect the overall effect of medical image generation, it means that the density of the metal is extremely small, and thus it is not necessary to perform artifact elimination processing thereto. Thus, an embodiment of the present invention determines whether or not it is necessary to perform artifact elimination processing to a medical image prior to performing artifact elimination processing to the image containing a metal region rather than performing artifact elimination processing to all images containing a metal region.

More specifically, according to an embodiment of the present invention, in the process of determining whether or not it is necessary to perform artifact elimination processing to a medical image, whether or not to perform artifact elimination processing to a medical image can be determined through comparing the obtained metal density value within a metal region with a preset density value. A detailed description is given in the following part in combination with FIG. 2.

It should be noted that the aforesaid artifact elimination processing is not limited to the manner shown in the embodiments of the present invention. It can be implemented by adopting any appropriate manners of artifact elimination processing. For instance, in an embodiment of the present invention, it can be implemented with the following steps: determining a metal region in a projection of a medical image, performing interpolation correction processing to the projection value within the metal projection region, and performing restoration and reconstruction processing to the medial image.

Figure 2:
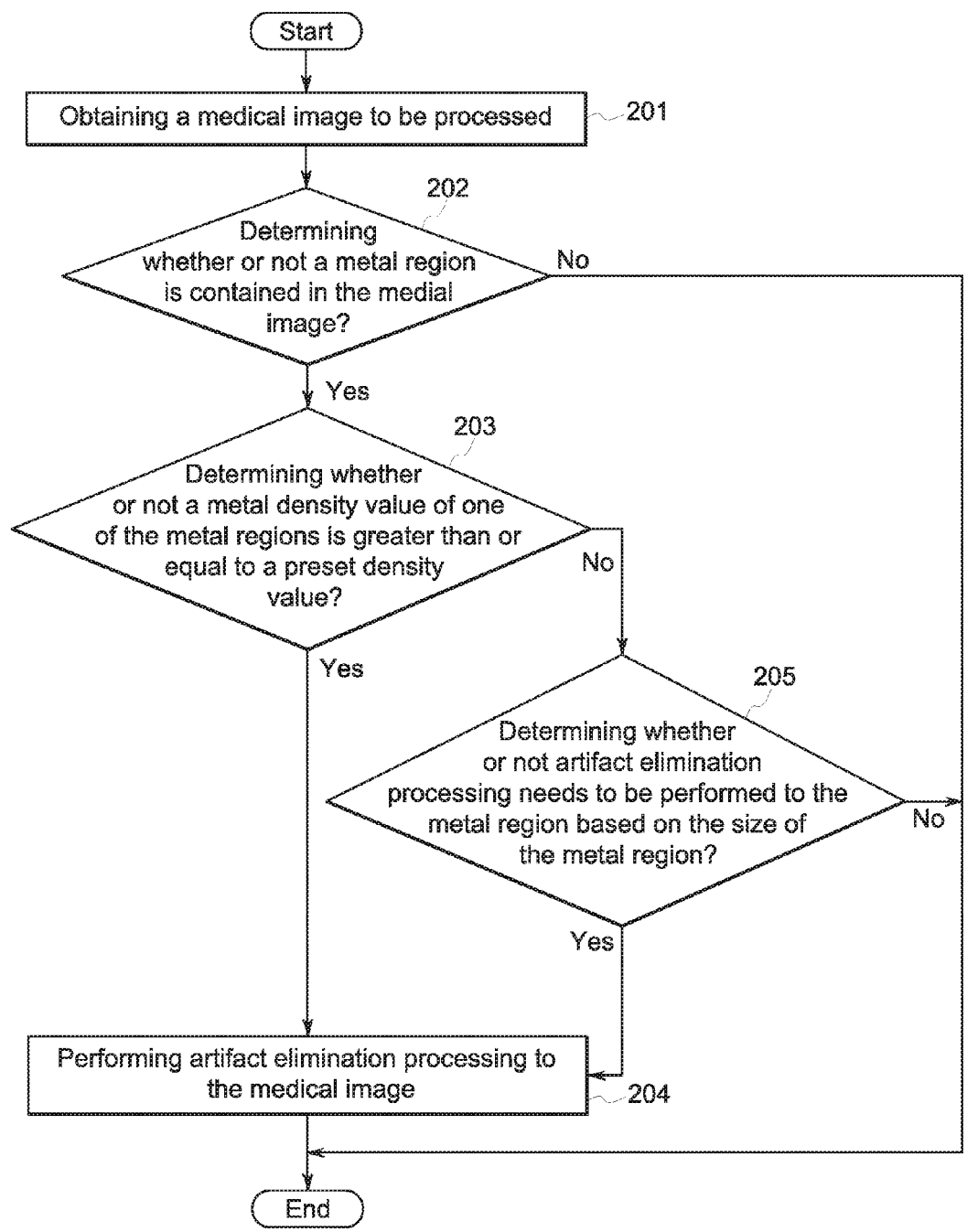
FIG. 2 shows a flow chart of another embodiment of the method for metal artifact elimination in a medical image according to the present invention.

Referring to FIG. 2, FIG. 2 shows a flow chart of the method for metal artifact elimination in a medical image according to another embodiment of the present invention, which describes the process of metal artifact elimination processing according to a more specific embodiment of the present invention.

As shown in FIG. 2, in step 201, obtaining a medical image to be processed. The step is similar to step 101 and is thus not repeated herein.

In step 202, determining whether or not a metal region is contained in the medial image.

Specifically, after obtaining a medical image to be processed, it is first determined whether or not a metal region is contained in the medical image. According to an embodiment of the present invention, pixel points in the obtained medical image can be scanned through setting a metal mask of a particular size, for instance. Upon scanning one or more pixel points having high pixel values in the medical image, the region in which these pixel points are contained can be indicated as a region having metal, i.e. a metal region. Thereafter, since the magnitudes of the pixel values at the position of the metal region are quite different from those of the pixel values within a non-metal region, a range of pixel values can be preset prior to determining the medical image, and then determining whether or not a metal region is contained in the currently obtained medical image through the pixel values in the preset range of pixel values. For instance, if the metal mask scans the pixel values of the current medical image (at this point, the scanned value is set to 5000) as greater than a minimum value of a preset pixel value (at this point, the minimum value is set to 4000), then it is determined that the currently scanned region of the medical image is a metal region. As for whether artifact elimination processing needs to be performed to a determined metal region, the detailed description can be seen in the analysis in steps 203-205.

Determination on whether a medical image contains a metal region is not limited to the aforesaid manner, but can be realized in any appropriate manner known in the art or to be developed in the future. For example, it can be realized in the manner of detector identification or projection region analysis, etc.

However, even if it is determined that a medical image contains a metal region, the final medical imaging is not always affected. For instance, if the metal density of a metal region is extremely small (e.g. when the scanned pixel value is 4000) or the metal region only occupies a very small range of the whole medical image (i.e. the metal region is only about 0.1% of the medical image), the artifact being generated will not affect the final medical imaging and generation of the medical image. Thus, further determination on the metal density in the metal region or the corresponding area being occupied needs to be made so as to reduce unnecessary artifact elimination processing and to enhance the display effect of the medical image.

Furthermore, if it is determined in step 202 that the medical image does not contain a metal region, then artifact elimination processing is not performed to the medical image, i.e. ending the processing.

If it is determined in step 202 that the medical image contains a metal region, then proceeding to step 203. At step 203, it is further determined whether a metal density value of one of the metal regions is greater than or equal to a preset density value.

Specifically, if a metal density value of one of the metal regions is greater than or equal to a preset density value, then proceeding to step 204. At step 204, artifact elimination processing is performed to the medical image.

If a metal density value of one of the metal regions is smaller than the preset density value, then proceeding to step 205. At step 205, determination on whether or not artifact elimination processing needs to be performed to the metal region is made based on the size of the metal region.

Specifically, since it has been determined the metal density value thereof is smaller than a preset density value, considering that the artifact generated by a metal region of a relatively large size will still affect the medical image itself, the size of the metal region thereof needs to be further determined to realize more reasonable artifact elimination processing.

For example, if a preset range of density values is [4000, 6000], the preset range of density values [4000, 6000] is embodied in the obtained medical image, which can be indicated as a gray value corresponding to a certain pixel position of the medical image. Furthermore, when an average gray value within a metal region scanned by a metal mask is smaller than a minimum value in the preset range, obviously, the artifact generated by the metal object does not affect the whole medical image; if an average gray value within a metal region is greater than or equal to a maximum value in the preset range, it means that the metal object has affected the final medical image generation effect in the whole medical imaging scan process. In this case, it is necessary to perform artifact elimination processing.

Furthermore, if an average gray value scanned in a metal region is 5000, which falls within the preset range of density values of [4000, 6000], the artifact generated thereby may affect the medical image effect, then corresponding artifact elimination processing is necessarily to be performed. Additionally, a further case is that the artifact generated thereby is insufficient to affect the final generating effect of the medical image, then unnecessary artifact elimination processing needs not to be performed. Moreover, when the detected average gray value of metal falls within the preset range of density values of [4000, 6000], the area proportion occupied by the pixels corresponding to a gray value generated by the metal in a medical image in the whole medical image should still be considered. Because even if the average gray value of the metal region thereof is small, if it occupies a relatively large area, it will still affect the effect of the final medical image generation. Thus, the size of the metal region thereof needs to be further determined.

If it is determined that the size of the metal region is larger than a preset size at step 205, then proceeding to step 204 to perform artifact elimination processing to the medical image. The result of determination herein shows that although the metal density thereof is small, an area of the artifact formed thereby is sufficient to affect the effect of the medical image, then it is necessary to perform the artifact elimination process.

Specifically, when the metal density value is within a preset range of density values, the size of area occupied by the metal region thereof in the medical image needs to be further determined, that is, determination on the distribution condition of the location of the pixel values having a metal density within the preset range of density values. For example, the size of the determined metal region is a metal region formed by 3*3 pixel values, and an average gray value in its metal region is 5000, and it occupies more than 3% of the pixel value position distribution in the whole medical image, then it will affect the final display effect of the medical image. At this time, only detecting a metal density value is obviously incomplete.

If it is determined at step 205 that the size of the metal region is smaller than a preset size, then terminating the processing to the medical image, i.e. not performing artifact elimination processing to the medical image. The result of determination herein means that even if a plurality of metal regions are present, if the metal density thereof is small and the metal region only occupies a small portion of the area of the whole medical image, that is, the artifact generated thereby is insufficient to affect the medical image, then it is unnecessary to perform artifact elimination processing any more at this time so as to avoid generating new obstacle factors (such as a new artifact).

Wherein the manner of artifact elimination processing is the same as that in FIG. 1, which is not repeated herein.

Figure 3:
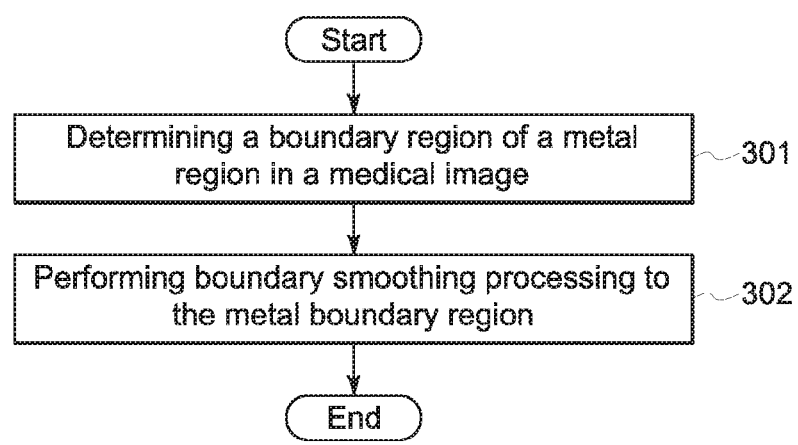
FIG. 3 shows a flow chart of an embodiment of boundary smoothing processing in the process of metal artifact elimination in a medical image according to the present invention.

Referring to FIG. 3, FIG. 3 shows a flow chart of boundary smoothing processing in the process of metal artifact elimination in a medical image according to an embodiment of the present invention.

As shown in FIG. 3, in step 301, determining a boundary region of a metal region in a medical image.

Figure 6A:
FIGS. 6A, 6B, and 6C are illustrative diagrams of results of metal artifact elimination processing and boundary smoothing processing according to an embodiment of the present invention.

Specifically, step 301 is a further enhanced processing after artifact elimination based on FIG. 1 and FIG. 2 to address the phenomenon of a new artifact generated after the artifact elimination or loss of details of the original image (e.g. a new artifact generated after the artifact elimination shown in FIG. 6A). More specifically, a boundary of a metal region (region to be processed) can be determined adaptively based on the size proportion of metal within a particular region such that the subsequent boundary smoothing processing can be more precise and thus a more precise and reasonable restoration and reconstruction can be performed to the metal region. The detail description thereof can be seen in the description of FIG. 4.

In step 302, boundary smoothing processing is performed to a boundary region of the metal. Boundary smoothing processing is performed to a boundary region of the metal because after the artifact elimination processing, modification and compensation need to be performed with regard to the problems of occurrence of a new artifact or loss of details of the medical image so as to ensure an undistorted medical image.

Figure 6B:
Figure 6C:

Specifically, as shown in FIGS. 6A-6C, wherein FIG. 6A is a currently scanned medical image, and since the density of the white bright metal region is too big, resulting in the gray value thereof is very high and the surrounding region is affected. Thus, a number of stripe-like artifact regions are formed (as indicated by the infrared arrow in FIG. 6A). After artifact processing, the effect thereof is as shown in FIG. 6B, wherein boundary blurring still occurs (as indicated by the infrared arrow in FIG. 6B). Thus, the blurred boundary position shown in FIG. 6B needs to be found and processed. Therefore, it is a key point to determine a region having a blurring boundary (referring to the description of FIG. 4). Upon determining a metal boundary region which needs to be processed, performing the boundary smoothing processing, and the effect thereof is as shown in FIG. 6C.

According to an embodiment of the present invention, boundary detection and wavelet algorithm, etc., can be used to perform boundary smoothing processing of a metal boundary region determined to be processed, but the present invention is not limited to these, instead, any appropriate manner known in the art or to be developed in the future can be used to perform the boundary smoothing processing. Detailed description about this step can be seen in step 404 shown in FIG. 4.

Figure 4:
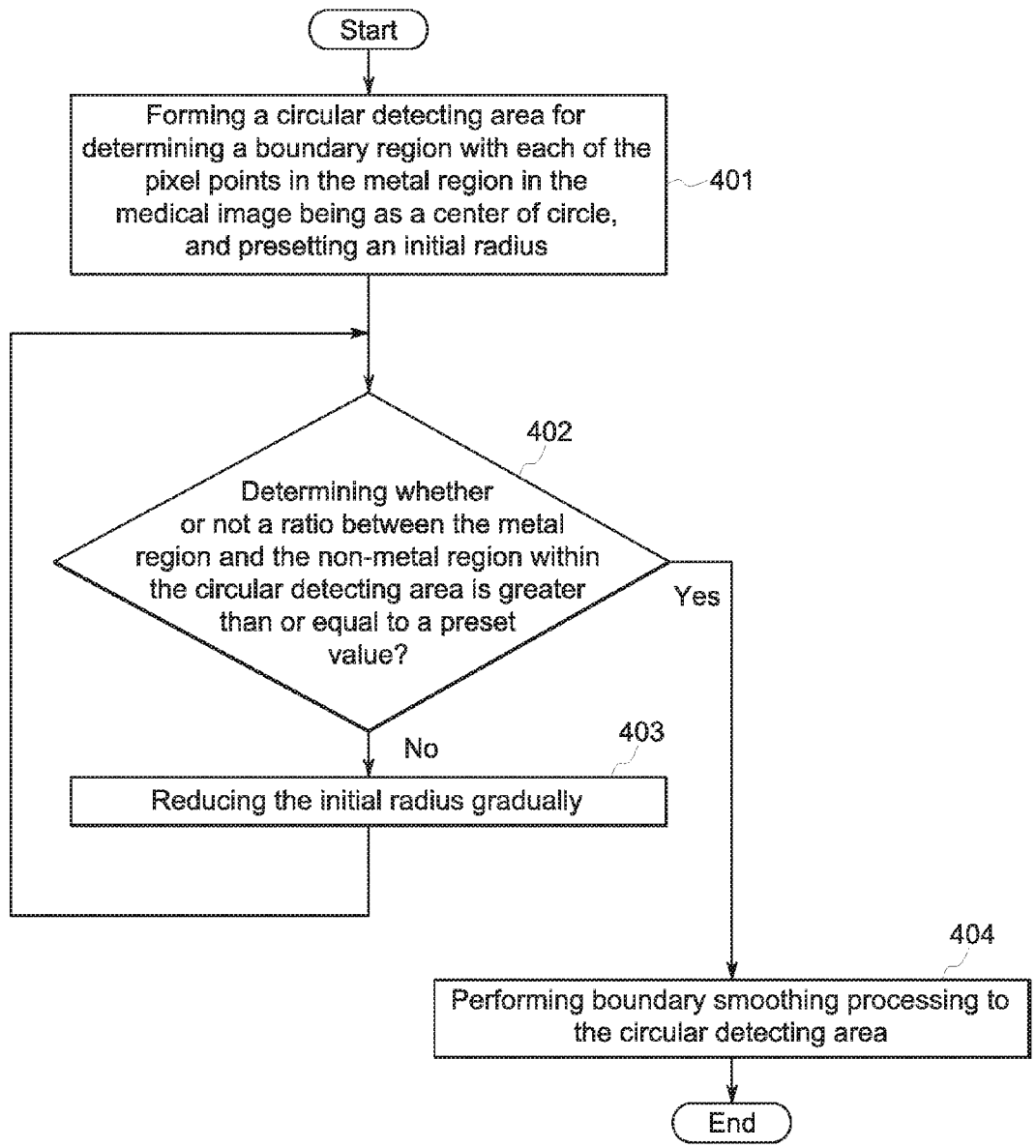
FIG. 4 shows a specific flow chart of determining a boundary of a metal region in a medical image according to an embodiment of the present invention.

Referring to FIG. 4, FIG. 4 shows a flow chart of determining a boundary region of a metal region in a medical image (step 301) according to an embodiment of the present invention.

As shown in FIG. 4, in step 401, a circular detecting area for determining a boundary region is formed with each pixel point in a metal region in a medical image being as a center of circle and presetting an initial radius.

According to an embodiment of the present invention, using each pixel point in the metal region (positions in the medical image are composed by a two-dimensional matrix) as the center of circle (set to be point O), and presetting an initial radius r=3 pixel widths, thereby one or more circular detecting areas are formed. Furthermore, the circular detection area proposed in embodiments of the present invention is substantively a pixel value corresponding to each pixel position in the scanning of the metal region, in this way, a metal boundary region which needs to be processed can be precisely determined.

In step 402, determining whether or not a ratio between the metal region and non-metal region within the circular detecting area is greater than a preset value.

Specifically, assuming the pixel c of the center of circle of the proposed circular detecting area is $(x_c, y_c)$, and the pixels k in the circular detecting area with point O as the center of circle and r as the radius is $(x_k, y_k)$.

Whereby, according to the embodiment of the present invention, assuming the number of pixels within the metal region in the circular detecting area is $D_c$, as shown in equation (1):

$$D_C = \{k | \sqrt{(x_c - x_k)^2 + (y_c - y_k)^2} <= r + 10^{-16}\} \quad (1)$$

then the number of pixels within the non-metal region in the circular detecting area is $D_n$, as shown in equation (2):

$$D_n = \{k \in D_C | f_k < t\} \quad (2)$$

wherein, $f_k$ is the number of pixels within the metal region, and t is a preset range of the number of pixels. That is, the non-metal region refers to the area except for the metal region within the circular detecting area.

According to an embodiment of the present invention, a ratio $$\frac{D_n - D_c}{D_n}$$

between the metal region and non-metal region within the circular detecting area can be obtained, and then it is determined whether $$\frac{D_n - D_c}{D_n} > T$$

is satisfied. Wherein T is a preset empirical value for determining a boundary of the metal region, e.g. T=0.5.

It should be noted that $$\frac{D_n - D_c}{D_n}$$

can be deemed as a ratio of the non-metal region in the circular detecting area. When a ratio of the non-metal region in the circular detecting area exceeds a particular threshold, it can be deemed a boundary region of the metal region has been determined.

If it is determined at step 402 that a ratio between the metal region and non-metal region within the circular detecting area is smaller than a preset value, then proceeding to step 403.

At step 403, reducing the initial radius gradually until a ratio between the metal region and non-metal region within the formed circular detecting area is greater than the preset value. For instance, the initial radius reduces gradually by one pixel width.

If it is determined at step 402 that a ratio between the metal region and non-metal region within the circular detecting area is greater than a preset value, then proceeding to step 404.

At step 404, performing boundary smoothing processing to the circular detecting area.

In an embodiment, the interpolation algorithm can be used to obtain a metal substitute value for replacing the pixel values of the pixels within the circular detecting area so as to complete the boundary smoothing processing of the metal region in the medical image. Specifically, based on the previously mentioned $D_c$, a proportion $F_c$ of the metal region within the circular detecting area can be calculated as follows:

$$F_c = \frac{\sum_{k \in D_c} f_k}{|D_c|} \quad (3)$$

Furthermore, an interpolation coefficient can be obtained based on $F_c$.

According to a specific embodiment of the present invention, the following interpolation equation can be obtained so as to obtain a metal substitute value:

$$I'_k = (1-F_c^4)\mu + F_c^4 m \quad (4)$$

Wherein $\mu$ is an average value of the reconstruction values of the pixels in $D_n$, and m is the metal value before the substitution.

When $D_n$ is 0, that is, there is only a metal region in the circular detecting area, then $\mu$ is set to m.

So far, a method for metal artifact elimination in a medical image according to the various embodiments of the present invention is described. According to the method of an embodiment of the present invention, unnecessary processing in the artifact elimination process can be avoided, and possibility of generating a new artifact can be reduced, thereby performing artifact elimination more reasonably and reducing distortion of a medical image. Similar to such method, an embodiment of the present invention further provides a corresponding apparatus.

Figure 5:
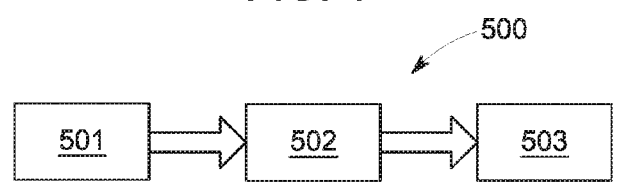
FIG. 5 shows an illustrative block diagram of an embodiment of the apparatus for metal artifact elimination in a medical image according to the present invention.

Referring to FIG. 5, FIG. 5 shows a block diagram of an apparatus for metal artifact elimination in a medical image according to an embodiment of the present invention.

As shown in FIG. 5, the apparatus 500 may comprise: an obtaining module 501, a metal region determining module 502 and a first artifact eliminating module 503.

Specifically, the obtaining module 501 can be used for obtaining a medical image to be processed.

The metal region determining module 502 can be used for determining whether or not a metal region is contained in the medial image.

The first artifact eliminating module 503 can be used for performing artifact elimination processing to the medical image when metal regions are contained in the medical image and a metal density value of one of the metal regions is greater than or equal to a preset density value.

According to an embodiment of the present invention, the apparatus 500 may further comprise a second artifact eliminating module for determining, when a metal region is contained in a medical image and a metal density value of one of the metal regions is smaller than a preset density value, whether or not artifact elimination processing needs to be performed to the metal region based on the size of the metal region.

According to an embodiment of the present invention, the first artifact eliminating module may comprise: a metal region determining module for determining a metal region in a projection of the medical image; an interpolation module for performing interpolation correction processing to pixels within the projection region; and an image reconstructing module for performing restoration and reconstruction to the medical image.

According to an embodiment of the present invention, the second artifact eliminating module may comprise: a metal region determining module for determining a metal region in a projection of the medical image; an interpolation module for performing interpolation correction processing to pixels within the projection region; and an image reconstructing module for performing restoration and reconstruction to the medical image.

According to an embodiment of the present invention, the apparatus 500 may further comprise: a boundary determining module for determining a boundary region of the metal region in the medical image; and a boundary processing module for performing boundary smoothing processing to the boundary region.

According to a more specific embodiment of the present invention, the boundary determining module may further comprise a circular detecting area forming sub-module and a boundary determining sub-module, wherein the circular detecting area forming sub-module is used for forming a circular detecting area for determining the boundary region with each of the pixel points in the metal region in the medical image being as a center of circle, and presetting an initial radius. The boundary determining sub-module is used for determining the circular detecting area is the boundary region if a ratio between the metal region and non-metal region within the circular detecting area is greater than or equal to a preset value, and if the ratio between the metal region and non-metal region within the circular detecting area is smaller than the preset value, reducing the initial radius gradually until the ratio between the metal region and non-metal region within the formed circular detecting area is greater than the preset value.

So far, an apparatus for metal artifact elimination in a medical image according to embodiments of the present invention is described. Similar to the aforesaid method, with the apparatus, artifact elimination can be performed more reasonably and distortion of a medical image can be reduced.

Since the processing of the apparatus for metal artifact elimination in a medical image corresponds to the processing of the method for metal artifact elimination in a medical image described in combination with FIGS. 1-4, regarding to the specific details thereof, references can be made to the method for metal artifact elimination in a medical image described above, which are not repeated herein.

As compared with the prior art, according to the technical solution of an embodiment of the present invention, determining whether an obtained medical image to be processed contains a metal region, and further analyzes a metal density value in the metal region and/or the size of the metal region when determining that a metal region is contained, whereby determining whether or not artifact elimination processing needs to be performed to the medical image. Accordingly, unnecessary processing in the process of artifact elimination can be avoided, and the possibility of generating a new artifact is reduced, and the artifact elimination processing is optimized, whereby a more accurate result is exhibited for the subsequent pathologic analysis.

Furthermore, according to the technical solution of an embodiment of the present invention, when it has been determined that a metal region is contained in the obtained medical image, and a metal density value of one of the metal regions is smaller than a preset density value, determination is made on whether or not artifact elimination processing needs to be performed to the medical image based on the size of the metal region so as to determine an artifact region that really needs to be processed. In the meanwhile, detail loss of image or generation of a new artifact after artifact processing is reduced through determining a boundary region of the metal region in the medical image and performing corresponding boundary smoothing processing to the boundary region.

What are described above are only embodiments of the present invention and are not used to limit the present invention. For those skilled in the art, there might be various modifications and changes to the present invention. Any modification, equivalent substitution and improvements within the spirit and principle of the present invention shall be included in the scope of claims of the present invention.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for metal artifact elimination in a medical image, operable in a medical imaging device, the method comprising:
    obtaining a medical image;
    determining a metal region in the medial image;
    determining a metal density value of the metal region; and
    performing an artifact elimination processing to the medical image when the metal density value of the metal region is greater than or equal to a preset density value, said artifact elimination processing comprising:
        determining a boundary region of the metal region as:
            forming a circular detecting area for determining a boundary region with each of the pixel points in the metal region being as a center of a circle, and presetting an initial radius;
            determining the circular detection area is the boundary region when a ratio between the metal region and the non-metal region within the circular detecting area is greater than or equal to a preset value, and
            reducing the initial radius gradually when the ratio between the metal region and the non-metal region within the circular detecting area is smaller than the preset value until the ratio between the metal region and non-metal region within the formed circular detecting area is greater than the preset value; and
        performing boundary smoothing processing to the boundary region.

2. The method according to claim 1 further comprising: when the metal density value of the metal region is smaller than a preset density value:
    determining whether the artifact elimination processing needs to be performed to the metal region based on the size of the metal region.

3. The method according to claim 2, wherein determining whether the artifact elimination processing needs to be performed comprises:
    performing the artifact elimination processing when the size of the metal region is greater than a preset size; and
    not performing the artifact elimination processing when the size of the metal region is smaller than a preset size.

4. The method according to claim 1, wherein performing artifact elimination processing to the medical image comprises:
    determining a projection region in the medical image;
    performing interpolation correction processing to an interpolation value in the projection region; and
    performing restoration and reconstruction processing to the medical image.

5. An apparatus for metal artifact elimination in a medical image, the apparatus comprising:
    a computer comprising:
        an obtaining module configured to obtain the medical image;
        a metal region determining module configured to determine a metal region in the medical image and a metal density value of the metal region; and
        a first artifact eliminating module configured to perform an artifact elimination processing on the medical image when the metal density value of the metal region is greater than or equal to a preset density value, said first artifact eliminating module comprising:
            a boundary determining module configured to determine a boundary region of the metal region, said boundary determining module comprising:
                a circular detecting area forming sub-module configured to form a circular detecting area determining a boundary region with each of the pixel points in the metal region being as a center of circle, and presetting an initial radius; and
                a boundary determining sub-module configured to determine the circular detecting area is the boundary region when a ratio between the metal region and non-metal region within the circular detecting area is greater than or equal to a preset value, and when the ratio between the metal region and non-metal region within the circular detecting area is smaller than the preset value, reducing the initial radius gradually until the ratio between the metal region and non-metal region within the formed circular detecting area is greater than the preset value;
            a boundary processing module configured to perform a boundary smoothing processing to the boundary region.

6. The apparatus according to claim 5 further comprising:
    a second artifact eliminating module configured to determine, when the metal density value of the metal region is smaller than a preset density value;
    determining whether the artifact elimination processing needs to be performed to the metal region based on the size of the metal region.

7. The apparatus according to claim 5, wherein the first artifact eliminating module comprises:

a metal region determining module configured to determine a metal region in a projection region of the medical image;
an interpolation module configured to perform an interpolation correction processing to pixels within the projection region; and
an image reconstructing module for performing restoration and reconstruction to the medical image.

8. An apparatus for metal artifact elimination in a medical image, the apparatus comprising:
a computer comprising:
an obtaining module configured to obtain the medical image;
a metal region determining module configured to:
determine at least one metal region in the medical image; and
a corresponding metal density value of for each of the at least one metal region; and
for each of the at least one metal region:
determining whether the metal density value of the metal region is greater than a preset density value;
for each of the at least one metal region having a metal density greater than the preset density value:
perform an artifact eliminating module comprising;
a boundary determining module configured to:
determine a boundary region of the metal region, said boundary determining module comprising:
a circular detecting area forming sub-module configured to:
form a circular detecting area determining a boundary region with each of the pixel points in the metal region being a center of a circle, and preset an initial radius; and
a boundary determining sub-module configured to:
determine the circular detecting area as the boundary region when a ratio between the metal region and non-metal region within the circular detecting area is greater than or equal to a second preset value, and
when the ratio between the metal region and non-metal region within the circular detecting area is smaller than the second preset value:
reducing the initial radius gradually until the ratio between the metal region and non-metal region within the formed circular detecting area is greater than the second preset value; and
a boundary processing module configured to:
perform a boundary smoothing processing to the boundary region.

* * * * *

UNITED STATES PATENT AND TRADEMARK OFFICE
CERTIFICATE OF CORRECTION

PATENT NO. : 9,437,017 B2  
APPLICATION NO. : 14/522783  
DATED : September 6, 2016  
INVENTOR(S) : Dong et al.

Page 1 of 1

It is certified that error appears in the above-identified patent and that said Letters Patent is hereby corrected as shown below:

On the Title Page

In Item (57), under "ABSTRACT", in Column 2, Line 4, delete "medial" and insert -- medical --, therefor.

In the Drawings

In Fig. 1, Sheet 1 of 5, for Tag "102", in Line 2, delete "medial" and insert -- medical --, therefor.

In Fig. 2, Sheet 2 of 5, for Tag "202", in Line 3, delete "medial" and insert -- medical --, therefor.

In the Specification

In Column 2, Line 3, delete "medial" and insert -- medical --, therefor.

In Column 4, Line 61, delete "medial" and insert -- medical --, therefor.

In Column 5, Line 5, delete "medial" and insert -- medical --, therefor.

In Column 9, Line 57, delete "medial" and insert -- medical --, therefor.

In the Claims

In Column 11, Line 43, in Claim 1, delete "medial" and insert -- medical --, therefor.

In Column 13, Line 17, in Claim 8, delete "value of for" and insert -- value of --, therefor.

Signed and Sealed this
Seventeenth Day of January, 2017

Michelle K. Lee
*Director of the United States Patent and Trademark Office*